United States Patent
Causier et al.

(10) Patent No.: US 10,365,236 B2
(45) Date of Patent: Jul. 30, 2019

(54) NMR MEASUREMENT CELL AND NMR MEASUREMENT ASSEMBLY

(71) Applicant: Commissariat A L'Energie Atomique et aux Energies Alternatives, Paris (FR)

(72) Inventors: Alexandre Causier, Gif sur Yvette (FR); Patrick Berthault, Magny les Hameaux (FR); Thomas Berthelot, Les Ulis (FR); Guillaume Carret, Villebon-sur-Yvette (FR)

(73) Assignee: Comissariat a l'energie atomique et aux energies alternatives, Paris (FR)

( * ) Notice: Subject to any disclaimer, the term of this patent is extended or adjusted under 35 U.S.C. 154(b) by 711 days.

(21) Appl. No.: 14/971,045

(22) Filed: Dec. 16, 2015

(65) Prior Publication Data
US 2016/0178544 A1    Jun. 23, 2016

(30) Foreign Application Priority Data
Dec. 19, 2014    (FR) ...................................... 14 62890

(51) Int. Cl.
*G01V 3/00*    (2006.01)
*G01N 24/08*    (2006.01)
(Continued)

(52) U.S. Cl.
CPC ......... *G01N 24/08* (2013.01); *G01R 33/0052* (2013.01); *G01R 33/30* (2013.01);
(Continued)

(58) Field of Classification Search
CPC .................................................... G01N 24/08
(Continued)

(56) References Cited

U.S. PATENT DOCUMENTS

| 5,397,989 A * | 3/1995 | Spraul .................. G01R 33/307 324/318 |
| 8,710,836 B2 * | 4/2014 | Adolphi ................. G01N 24/08 324/303 |
| 9,139,862 B2 | 9/2015 | Berthelot et al. |
| 2011/0285396 A1 | 11/2011 | Hofmann et al. |

FOREIGN PATENT DOCUMENTS

EP    1 901 782    3/2008

OTHER PUBLICATIONS

French Preliminary Search Report dated Oct. 9, 2015 in French Application 14 62890, filed on Dec. 19, 2014 ( with English translation of Categories of Cited Documents).
(Continued)

*Primary Examiner* — Louis M Arana
(74) *Attorney, Agent, or Firm* — Oblon, McClelland, Maier & Neustadt, L.L.P.

(57) ABSTRACT

There is provided a Nuclear Magnetic Resonance (NMR) measurement cell for use with a solution enabling the introduction of a gas into said solution. The measurement cell includes at least a detection volume designed to be installed in a static magnetic field of an NMR spectrometer, and includes in said detection volume, a gas introduction zone, a measurement chamber for the solution at a distance from the gas introduction zone and a network of conduits for the solution formed to set up fluid communication between the gas introduction zone and the measurement chamber. The gas introduction zone includes at least one gas inlet in the network of conduits, to generate bubbles in the gas introduction zone only. There is also provided a method of manufacturing such a measurement cell and a measurement assembly including such a measurement cell.

14 Claims, 5 Drawing Sheets

(51) Int. Cl.
*G01R 33/30* (2006.01)
*G01R 33/46* (2006.01)
*G01R 33/00* (2006.01)
*G01R 33/28* (2006.01)

(52) U.S. Cl.
CPC .......... *G01R 33/302* (2013.01); *G01R 33/46* (2013.01); *G01R 33/282* (2013.01)

(58) Field of Classification Search
USPC ........................................ 324/318, 319, 321
See application file for complete search history.

(56) References Cited

OTHER PUBLICATIONS

Roger M. Bourne "A Device for Aeration and Mixing of Cell and Organelle Suspensions During Nuclear Magnetic Resonance Studies", Analytical Biochemistry, vol. 182, No. 1, 1989, 6 pages.

G. S. Karczmar et al. "A Device for Maintain Viable Cells At High Densities for NMR Studies", Journal of Magnetic Resonance, vol. 53, No. 1, 1983, 6 pages.

Zackary I. Cleveland et al. "Continuously Infusing Hyperpolarized $^{129}$Xe Into Flowing Aqueous Solutions Using Hydrophobic Gas Exchange Membranes", The Journal of Physical Chemistry, vol. 113, No. 37, 2009, 11 pages.

Mark Sankey et al. "Sprite MRI of bubbly flow in a horizontal pipe", Journal of Magnetic Resonance, vol. 199, 2009, 10 pages.

Kai Ruppert "Biomedical imaging with hyperpolarized noble gases", Reports on Progress in Physics, vol. 77, No. 11, 2014, 34 pages.

U.S. Appl. No. 12/772,122, filed Apr. 30, 2010, 2010/0311857 A1, Thomas Berthelot et al.

U.S. Appl. No. 13/514,963, filed Dec. 10, 2010, 2012/0282417 A1, Alexandre Garcia et al.

U.S. Appl. No. 14/005,116, filed Mar. 21, 2012, 2014/0044884 A1, Thomas Berthelot et al.

U.S. Appl. No. 14/365,377, filed Dec. 14, 2012, 2014/0349279 A1, Thomas Berthelot et al.

\* cited by examiner

NMR MEASUREMENT CELL AND NMR MEASUREMENT ASSEMBLY

TECHNICAL DOMAIN

This invention relates to spectroscopy by Nuclear Magnetic Resonance, better known as NMR, and the possibility of performing spectroscopy or imagery on a solution with the introduction of gas.

STATE OF PRIOR ART

In general, gases are introduced into solutions for NMR measurements independently of NMR measurement phases to make sure that gas is well diluted in the solution and to prevent this introduction from disturbing measurements due to the presence of bubbles that could cause losses of uniformity in the magnetic field. This introduction before the measurement may for example be made by stirring the solution in the presence of gas and will generally be combined with liquid circulation to assure that the solution is uniform. Furthermore, due to spectrometer space constraints, the gas is introduced by stirring «outside magnet» in the leakage field of the NMR spectrometer magnet.

Therefore, the result with this usual configuration is that although measurement cells allowing such an introduction of gas are compatible with conventional NMR spectrometers, they nevertheless require a significant circulation of solution to transfer gas as far as the spectrometer detection volume, and therefore a large quantity of solution. Therefore, this increases the cost of making such measurements on solutions to be measured that are expensive to obtain. Furthermore, with this type of introduction «outside magnet» and «outside a measurement period», it is difficult to use gases with non-equilibrium magnetic properties that cannot be maintained without the static magnetic field of the magnet of the NMR spectrometer.

Cleveland Z. I. and his assistants developed an adapted measurement cell to solve this problem and thus make an NMR measurement possible on a solution with significant gas introduction during the measurement and under the static magnetic field of the NMR spectrometer. This measurement cell is described in their article published in the «Journal of Physical Chemistry B» vol 113 (27) pages 12489 to 12499 published on Sep. 17, 2009 and in particular is illustrated in FIG. 1 in this article. Such a cell comprises the following within the detection volume of the cell that is placed in the static magnetic field of the NMR spectrometer during the measurement:
  a gas exchanger module, similar to that described in document EP 1901782 B1;
  a measurement chamber to which a radiofrequency electromagnetic field is applied;
  a network of conduits between the gas exchanger module and the measurement chamber.

The gas exchanger module is in the form of a network of membranes delimiting transfer channels for gases between which the solution circulates, to avoid disturbing the NMR measurement. These membranes are partially leak tight to allow gas to pass into solution while preventing the solution from penetrating into the gas transfer channels. The cell also comprises an extension to the network of conduits outside the detection volume in which a pumping system is provided to circulate the solution between the measurement chamber and the gas exchanger module, so that the solution can be circulated between the module and the measurement chamber.

Thus, although this type of cell can be used to make an NMR measurement on a solution with a significant gas introduction into the solution under the static magnetic field of the NMR spectrometer, it does have some disadvantages.

The dimensions of this gas exchanger module necessary to introduce a significant amount of gas into solution are not compatible with conventional NMR spectrometers. Thus, Cleveland Z. I. and his assistants had to use an MRI designed for small animals with a 10 cm diameter housing and therefore capable of containing large cells, in order to make the NMR measurement. Obviously, the frequency resolution with such an MRI is necessarily not as good as with a conventional NMR spectrometer. Furthermore, it should be noted that the configuration chosen by Cleveland Z. I. and his assistants has the disadvantage of being expensive in terms of the solution to be analysed and gas, particularly due to the use of an external reservoir at a distance of 2.4 m from the measurement zone and a peristaltic pump.

For applications to biological cells that require an oxygen supply throughout the measurement, Bourne has also disclosed an aeration device to be placed in an NMR sample test tube, as part of his work published in 1989 in the «Analytical Biochemistry» scientific review Vol. 182 pages 151-156. Such a device comprises a lower tube called a «draft tube» delimiting the measurement zone that will be subjected to the reception coil during the NMR measurement and a device casing inside which a conduit is formed in fluid communication with the lower tube. Said conduit comprises a gas introduction zone in which a gas inlet is formed to generate bubbles in the gas introduction zone only.

Although such a device can be used to introduce gas into solution with a particularly low risk of the presence of bubbles in the measurement zone, it cannot be used to introduce gas efficiently and does not seem very compatible with a liquid circulation system. Gas is only introduced by diffusion of gas from the introduction zone to the measurement zone, and this diffusion remains contained particularly due to a small diameter conduit setting up communication between these two zones. Furthermore with such a device, liquid will be circulated through side channels and therefore outside the test tube, and the small amount of gas introduced through the introduction zone will then be evacuated by circulation of the solution. Thus, the device disclosed by Bourne does not seem very efficient and would not be appropriate if circulation of the solution in the static magnetic field of the NMR spectrometer is required particularly to obtain a homogeneous solution, particularly for dilution of gas in solution.

PRESENTATION OF THE INVENTION

The invention is intended to at least partially overcome these disadvantages and thus particularly to provide a cell for making an NMR measurement in solution that can provide circulation of the solution without disturbing the introduction of gas and is compact so that it is suitable for use with conventional spectrometers for which the diameter of the detection zone is usually smaller than 2 cm, while allowing for a significant gas quantity to be introduced into the detection volume of the cell without disturbing the measurement.

Another purpose of the invention is to provide an NMR cell allowing for fluid circulation only in the measurement cell without the use of a mechanical and/or electromagnetic element that could disturb the static magnetic field of the NMR spectrometer.

To achieve this, the invention relates to a Nuclear Magnetic Resonance (NMR) measurement cell in solution enabling the introduction of a gas into said solution, the measurement cell being designed to be placed in a static magnetic field such as the field of an NMR spectrometer, and comprising:

- at least one measurement chamber of the solution in which a radiofrequency electromagnetic field will be applied and/or measured;
- at least one conduit for the solution in fluid communication with the measurement chamber, said conduit comprising a gas introduction zone comprising a gas inlet to generate bubbles only in the gas introduction zone;

the measurement cell also comprising:

- a network of conduits including at least one conduit and forming a closed circuit for circulation of the solution between the measurement chamber and the gas introduction zone, the gas inlet being arranged so as to set up circulation of the solution in the network of conduits between the gas introduction zone and the measurement chamber, the measurement chamber comprises a conduit in the network of conduits called the measurement conduit;
- a radiofrequency system arranged to apply and/or detect a radiofrequency electromagnetic field in the measurement conduit.

Due to the introduction of gas by means of gas bubbles generated directly in the network of conduits, such a measurement cell, enables efficient introduction of gas without requiring a large gas exchanger module, unlike the cell developed by Cleveland Z. I. and his assistants. The result is that the dimensions of a measurement cell according to the invention can be limited and can be compatible with cavities in conventional spectrometers, in other words with a diameter of less than 2 cm. Furthermore, NMR measurements are not disturbed by the introduction of gas since bubbles are generated in a part of the network of conduits distinct from the measurement chamber.

Furthermore, a network of conduits that forms a closed solution circulation circuit can achieve circulation of the solution in the network of conduits between the gas introduction zone and the measurement chamber simply by introducing gas. Therefore, there is no need to provide a system for pumping the solution to circulate it in the cell and to make it homogenous. In this way, such a cell can thus include the entire solution circulation system within a small volume compatible with conventional spectrometers, with efficient introduction of gas into solution and setting up circulation to achieve uniform gas dissolution throughout the entire solution, and particularly in the measurement chamber. Therefore, such a cell can be used to make NMR measurements in solution with efficient introduction of gas, that are perfectly resolved and stable in time, while being compatible with introduction of gas with non-equilibrium magnetic properties, using a conventional NMR spectrometer.

Therefore, such a cell is particularly advantageous when a solution has to be circulated to prevent stagnation of the solution in the measurement chamber that would be prejudicial to the NMR measurement, without requiring a large quantity of solution as is the case in prior art requiring a circulation and pumping system external to the measurement cell.

In the above and throughout the remainder of this document, the expression measurement of a radiofrequency electromagnetic field means measurements of any radiofrequency electromagnetic signals whatsoever, including electromagnetic disturbances generated by spin noise.

A Nuclear Magnetic Resonance measurement cell in solution obviously means a cell or vessel that can be used to make an NMR measurement in solution, in other words a liquid medium, to characterise all species present in said solution.

In the above and throughout the remainder of this document, the expression "solution closed circuit" means that there is no inlet or outlet for the solution in the network of conduits under measurement conditions, thus the solution circulates in a closed circuit. It should be noted that obviously, this does not exclude the possibility that the network of conduits might comprise several circulation branchs in parallel and/or in series, included within the detection volume.

The gas introduction zone may also comprise a gas outlet in fluid communication with the network of conduits that is intended to be outside the solution.

With such a gas outlet, bubbles come out of solution before the gas thus released can be evacuated through the gas outlet that is outside the solution. This thus avoids the risk of presence of gas bubbles in the measurement chamber that could disturb the NMR measurement.

The measurement chamber may be configured such that the ratio between the circulation distance of the solution from the measurement chamber to the gas inlet and the circulation distance from the gas outlet to the measurement chamber in the conduit circuit of the measurement chamber is less than 1, and is preferably less than 0.5 and even more preferably less than 0.2.

In the above and throughout the remainder of this document, the expression "circulation distance of the solution" between two parts of the measurement cell connected to each other through the circulation network means the length of the conduit connecting said parts.

With such a ratio of circulation distances, the measurement chamber is located at a relatively long distance from the gas introduction zone along the direction of circulation of the solution. This thus limits risks of undissolved bubbles in solution being present in the measurement chamber and therefore the resulting measurement disturbances.

The measurement cell may comprise a base for its installation in an NMR spectrometer defining a base plane, and the gas introduction zone may comprise a conduit called the gas introduction conduit in the network of conduits, that extends transverse or even approximately perpendicular to the base plane, the gas inlet being located in the gas introduction conduit closer to the base than the gas outlet.

With gas being introduced at the base in a transverse conduit, preferably perpendicular to the base plane, the bubbles benefit fully from the buoyant force of the Archimedes' principle during their path from the gas inlet to the gas outlet. Their displacement velocity thus increased by the Archimedes thrust has an influence on setting up circulation. Thus, such a cell enables efficient continuous circulation of the solution in the circulation network.

The measurement cell may comprise a gas conveyance conduit in the gas introduction conduit, a first end of which opens up into the gas introduction conduit and forms the gas inlet.

With such a conduit, all branch connections of the cell to a gas supply network may be made on the top of the cell. This facilitates the connection of the cell.

The gas introduction conduit can open up into a gas extraction area of which a first part delimits a conduit in the network of conduits and a second part will be outside solution, the gas outlet being located in said second part.

The measurement cell may comprise a radiofrequency system formed in the measurement zone to apply and/or detect a radiofrequency electromagnetic field in the measurement chamber.

The measurement cell may comprise a casing made in two portions, a first portion forming a base for installation of the measurement cell in an NMR spectrometer and in which the measurement chamber is formed, and a second portion comprising the gas introduction zone, said first and second portion having complementary shapes such that the network of conduits is formed by the assembly of the first and the second portion.

The first portion may comprise a first and a second element, the first element forming the external casing of the first portion, the second element comprising the measurement chamber and the radiofrequency system.

Such a cell design makes it possible to adapt the material in each part of the cell to satisfy NMR measurements constraints, without drastically increasing the manufacturing cost of the cell. Thus for example, a second element of the first portion can be made from glass, to limit risks of disturbing the NMR measurement, and the first element of the first portion and the second portion can be made from plastic that is easier to use and less expensive.

The measurement cell may be sized so that it can be placed in a static magnetic field such as the magnetic field of an NMR spectrometer, the entire measurement cell thus forms the detection volume.

Such a configuration facilitates installation of the cell in an NMR spectrometer.

The measurement cell may also comprise a filtration system in the gas introduction zone formed in the network of conduits to intercept gas bubbles at the outlet from the gas introduction zone along the direction of circulation of the solution.

The filtration system may comprise a filtration grid with a mesh size smaller than 1 mm or even 0.5 mm.

Such filtration systems enable better introduction of gas into solution and therefore higher circulation velocities in the network of conduits without a risk that this better introduction and this higher velocity will increase the risk of bubbles being present in the measurement chamber. Similarly, risks of the presence of bubbles outside the introduction zone that could cause blockage of conduits in the network of conduits outside this zone, can be avoided. It is therefore possible to provide relatively small conduit diameters for these conduits outside the introduction zone, and therefore to correspondingly reduce the solution quantity necessary for the measurement cell according to the invention.

The measurement cell may comprise:
  a base for its installation in an NMR spectrometer defining a base plane;
  at least two conduits, a first conduit so-called gas introduction conduit, and a second conduit both extending transversally, or even approximately perpendicular to the base plane, the gas introduction conduit comprising a gas inlet to form bubbles in the first conduit and thus form the gas introduction zone;
  at least a third and a fourth conduit connecting the first and second conduits at their ends located close to the base and at a distance from the base respectively, so as to form a closed circulation circuit for the solution and thus form the network of conduits;
  the radiofrequency system formed in the measurement zone to apply and/or detect a radiofrequency electromagnetic field in a portion of the third conduit so as to define a measurement chamber.

The invention relates to a method of manufacturing a measurement cell comprising the following steps:
  provide a radiofrequency system;
  provide a conduit in which the measurement will be made, to form the measurement conduit;
  position the radiofrequency system relative to the measurement conduit such that the radiofrequency system can apply and/or detect a radiofrequency electromagnetic field in the measurement conduit (23) so as to form a measurement chamber;
  provide additional conduits to form a network of conduits with the measurement conduit, said network of conduits including a conduit for the solution in fluid communication with the measurement chamber, said conduit comprising a gas introduction zone comprising a gas inlet to generate bubbles in the gas introduction zone only, the network of conduits forming a closed circuit for circulation of the solution between the measurement chamber and the gas introduction zone, the gas inlet being positioned so as to cause circulation of the solution in the network of conduits between the gas inlet zone and the measurement chamber;
  form the measurement cell by assembling the additional conduits with the assembly formed during positioning of the radiofrequency system relative to the measurement conduit, the measurement chamber comprises a conduit in the network of conduits, called the measurement conduit.

Such a manufacturing method can be used to obtain a cell according to the invention.

The step to provide additional conduits to form a network of conduits with the measurement conduit may consist of providing the network of conduits, excluding a conduit inside the measurement chamber, the gas inlet being formed in said network of conduits, said additional conduits forming a first element;

the step to position the radiofrequency system relative to the measurement conduit such that the radiofrequency system of the measurement chamber consisting of forming a second element including the conduit inside the measurement chamber and a radiofrequency system capable of generating et/or measuring a radiofrequency field;

the step to form the measurement cell consisting of assembling the network of conduits, excluding the conduit inside the measurement chamber, with the second element including the conduit inside the measurement chamber.

As a variant, the invention also relates to a method of manufacturing a measurement cell comprising the following steps:
  provide a gas introduction zone comprising a gas inlet into a conduit;
  provide at least one measurement chamber of the solution in which a radiofrequency electromagnetic field will be applied and/or measured;
  form a network of conduits for the solution, positioned to put the measurement chamber into fluid communication with the gas inlet zone, said network of conduits including the conduit in which the gas inlet is located.

Such a manufacturing method can be used to make a cell according to the invention.

The step to provide the gas introduction zone may consist of providing the network of conduits, excluding a conduit inside the measurement chamber, the gas inlet being positioned in said network of conduits.

The step to provide the measurement chamber may consist of providing a second element comprising the conduit included in the measurement chamber and a radiofrequency system capable of generating and/or measuring a radiofrequency field.

The step to form the network of conduits may consist of assembling the network of conduits, excluding the conduit inside the measurement chamber, with the second element including the conduit inside the measurement chamber.

With such steps to provide or form the gas introduction zone of the measurement chamber and the network of conduits, it is possible to make a cell using different materials, such as glass or quartz for the measurement chamber and plastic for the remaining part of the cell. It thus becomes feasible to reduce the manufacturing cost of such a cell while respecting imposed material constraints for the measurement chamber for NMR measurements.

The invention also relates to a Nuclear Magnetic Resonance (NMR) measurement assembly in solution comprising:
an NMR spectrometer, or equivalent, suitable for generating a first static magnetic field, and
an NMR measurement cell in solution,
a gas introduction system,
the measurement cell being a cell according to the invention with its gas inlet connected to the gas introduction system.

Such an assembly including a cell according to the invention has the advantages inherent to this cell that have been described above.

BRIEF DESCRIPTION OF THE DRAWINGS

This invention will be better understood after reading the description of example embodiments, given purely for information and in no way limitative, with reference to the appended drawings in which.

Identical, similar or equivalent parts of the different figures have the same numeric references so as to facilitate comparisons between different figures.

Figure 1A:
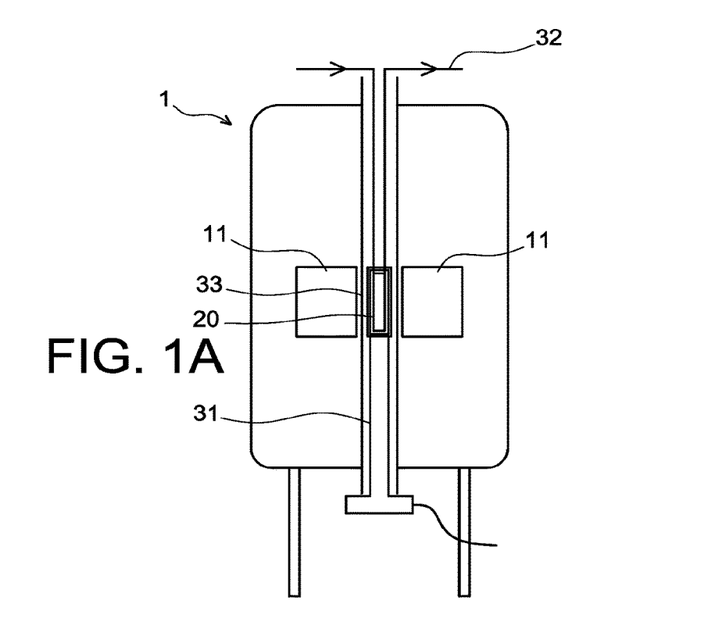
FIGS. 1A and 1B show two diagrammatic views of an NMR spectrometer equipped with a measurement cell according to the invention, and a measurement cell according to the invention.

The different parts shown in FIGS. 1A and AB are not necessarily at the same scale, to make the figures easier to understand. FIGS. 4A and 4B, and FIGS. 5A and 5B, have been drawn to scale.

The different possibilities (variants and embodiments) must be understood as not being exclusive to each other and can be combined with each other.

DETAILED PRESENTATION OF PARTICULAR EMBODIMENTS

FIG. 1A shows an example of an NMR measurement setup comprising a standard NMR magnet 1 and a measurement cell 20 according to the invention in which a solution 33 to be analysed has been introduced, said measurement cell 20 being arranged so that the static magnetic field of the NMR magnet is applied to it. The static magnetic field 20 shown in FIG. 1A is configured by the coil system 11 used to generate it.

In the configuration shown in FIG. 1, since the measurement cell 20 is arranged so that its entire volume is affected by the static magnetic field of the NMR magnet, the entire cell forms a detection volume placed in the static magnetic field of the NMR magnet 1.

Figure 1B:
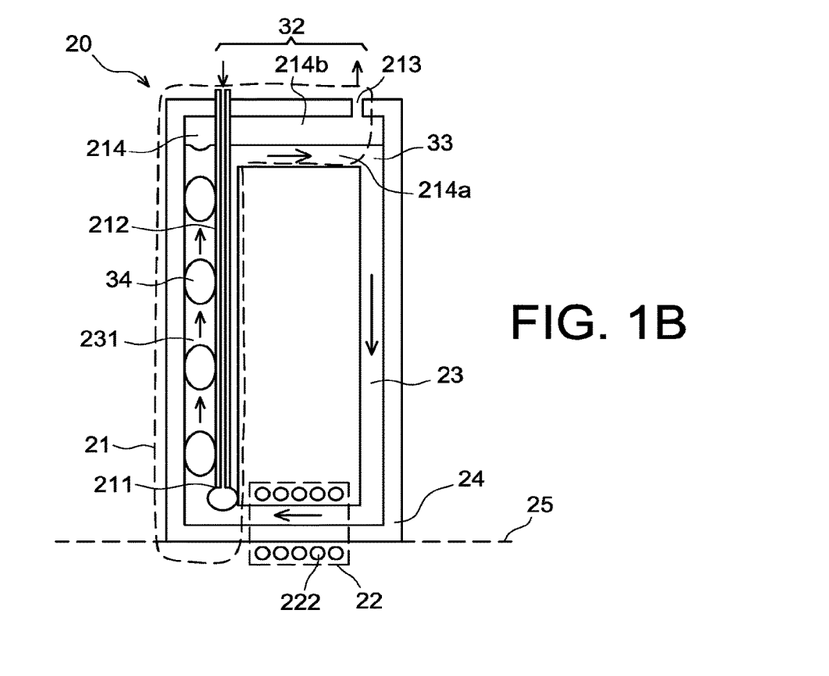

The measurement cell 20 shown in FIG. 1B comprises:
an introduction gas zone 21 in into solution 33 in which there is a gas inlet 211 and a gas outlet 213, positioned so that gas bubbles 34 can be generated only in the gas introduction zone;
at least one measurement chamber 22 of the solution 33 in which a radiofrequency electromagnetic field is applied and/or measured during the NMR measurement, the measurement chamber 22 being at a distance from the gas introduction zone 21;
a network of conduits 23 for the solution 33 positioned to bring the measurement chamber 22 into fluid communication with the gas introduction zone 20;
a base 24 through which the measurement cell bears in a housing in the NMR spectrometer, said base delimiting a base plane for the cell in said housing.

It can be seen more precisely in FIG. 1B that the gas introduction zone 21 comprises a conduit 231 in the network of conduits 23, called the gas introduction conduit. The gas introduction conduit 231 extends approximately perpendicular to the base plane 25 with the gas inlet 211 located in the gas introduction conduit 231 close to the base 24 relative to the gas outlet 213. It can thus be seen in FIG. 1B that the gas inlet 211 is located in the lower part of the gas introduction conduit 231.

According to one variant of the invention, not shown, the gas introduction conduit 231 may also extend approximately transverse relative to the base plane 25. Thus, although it is preferable that the gas introduction conduit 231 should extend along a direction at a significant slope relative to the base plane, said slope can nevertheless be between 10 and 90° without going outside the scope of the invention.

In order to supply the gas inlet 211 in the gas introduction conduit 231, the measurement cell 20 also comprises a gas conveyance conduit 212 in the gas introduction zone 21, located in the gas conduit 231 with a first end that opens up in gas conduit 231. The opening of the first end of the gas conveyance conduit 212 thus forms the gas inlet 211. The second end of the gas introduction conduit 212 communicates with the outside of the conveyance cell 20 so as to enable connection of the gas conveyance conduit 212 to a gas supply network 32 such as a supply network of hyperpolarised xenon or helium 3. Such a gas supply network 32 forms a gas introduction system.

The diameter of the gas conveyance conduit is similar to the diameter of the gas introduction conduit 231 so as to counterbalance head losses induced by a small diameter and the volume occupied by the gas conveyance conduit 21. Typically, the outside diameter of the conveyance conduit 21 may be between 1.2 times and 1.5 times less than the inside diameter of the gas introduction conduit 231.

In order to extract the gas introduced through the gas inlet 211, the measurement cell 20 also comprises a gas extraction area 214 in the gas introduction zone 21, a first part 214*a* of which delimits a conduit in the network of conduits 23 and a second part 214*b* is outside the solution. The gas outlet 213 is located in said second part 214*b* and is thus in fluidic communication with the network of conduits 23 through the extraction area 214.

The extraction area 214 and therefore the gas introduction zone 21, are in fluidic communication with the measurement chamber 23 through the network of conduits 23 such that the measurement chamber 22 can be supplied with gas through the introduction of gas in the gas introduction zone 231.

As shown in FIG. 1B, the measurement chamber 22 may be formed by a conduit in the conduit circuit 23, by providing a means in the measurement cell 20 adapted to generate and/or measure a radiofrequency electromagnetic field in said conduit. Such a means of generating and/or measuring an electromagnetic field may be provided by a coil system 222 such as a solenoid, a saddle-shaped coil, a Helmholtz coil or a bird cage coil, adapted as shown in FIG. 1B. More generally, such a means is called a radiofrequency system.

The measurement chamber is arranged such that the ratio of solution 33 circulation distances in the conduit circuit from the measurement chamber to the gas inlet 211 and from the gas outlet 213 to the measurement chamber 23 is less than 1, and is preferably less than 0.5 and is even more preferably less than 0.2. Thus, this ratio is about one seventh in the configuration shown in FIG. 1B.

The gas introduction zone 21 is put into communication with the measurement chamber 22 through the network of conduits 23 such that the network of conduits forms a closed circuit for circulation of the solution 33.

With such a configuration of the measurement cell 20, when gas is introduced through the gas inlet 211, it forms bubbles 34 in the gas introduction conduit 231 that emerge in the second part 214*b* of the extraction area 214. This emersion of bubbles 34 in the second part 214*b* of the extraction area 214 introduces gas that is recovered through the gas outlet 213. Therefore, the result is that bubbles 34 are generated and transit only in the gas introduction conduit 231 and the first part of the extraction area 214, since no bubbles 34 are generated in the remainder of the network of conduits 23. Good gas dissolution in the solution 33 is obtained by bringing gas bubbles 34 into contact with the solution 33 in the gas introduction conduit 231, without this gas introduction into solution 33 disturbing the measurement chamber 22.

The movement of each bubble in the gas introduction zone 21 generates a negative pressure in the gas introduction conduit 231 so that the solution 33 moves in the network of conduits 23. Thus, injection of gas in the gas introduction zone 21 enables circulation of the solution 33 in the network of conduits 23 between the gas introduction zone 21 and the measurement chamber 22.

Therefore, such a measurement cell 20 makes it possible to obtain dissolution of gas in solution in the static magnetic field of the NMR spectrometer and movement of the solution 33 in the small volume of the housing of a conventional NMR spectrometer, without the NMR measurement in the measurement chamber 20 being disturbed.

It should be noted that, as an alternative and in addition to the description of the measurement cell according to the invention given above, the measurement cell 20 according to the invention comprises:

the base 24 for its installation in an NMR spectrometer 1 defining a base plane 25;

at least two conduits, a first conduit 231 called the gas introduction conduit, and a second conduit 232 both of which extend transversally, or even approximately perpendicularly to the base plane 25, the gas introduction conduit 231 comprising a gas inlet so as to form bubbles in the first conduit and thus form the gas introduction zone;

at least a third and a fourth conduit 233, 234 connecting the first and the second conduit at their ends, located close to the base and at a distance from the base respectively, so as to form a closed circuit for circulation of the solution and thus form the network of conduits;

the radiofrequency system 222 located in the measurement zone to apply and/or detect a radiofrequency electromagnetic field in a portion of the third conduit so as to define the measurement chamber 22.

Figure 2A:
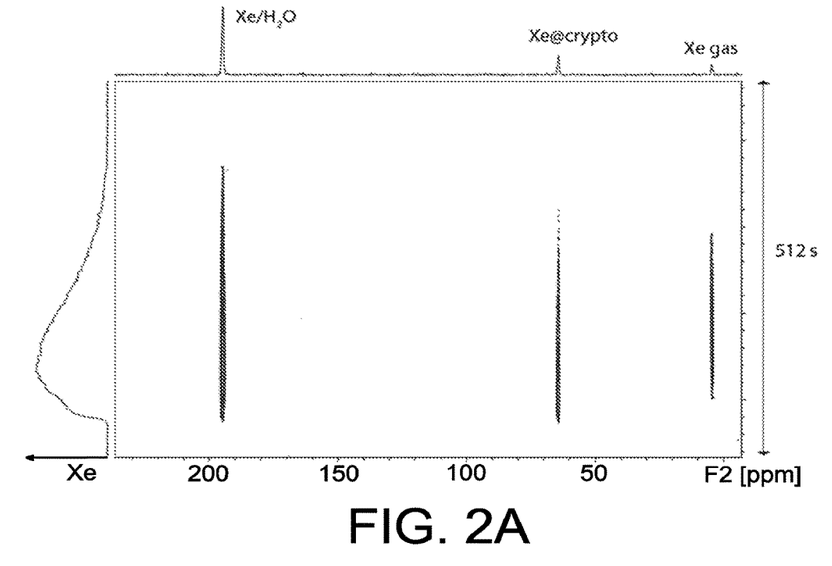
FIGS. 2A and 2B show two NMR measurements made on a solution of cryptophanes into which a hyperpolarised Xenon gas is introduced, the introduction being made for the spectra in FIGS. 2A and 2B respectively, by stirring according to a prior art's method and by the formation of bubbles using a measurement cell like that diagrammatically shown in FIG. 1B.
Figure 2B:
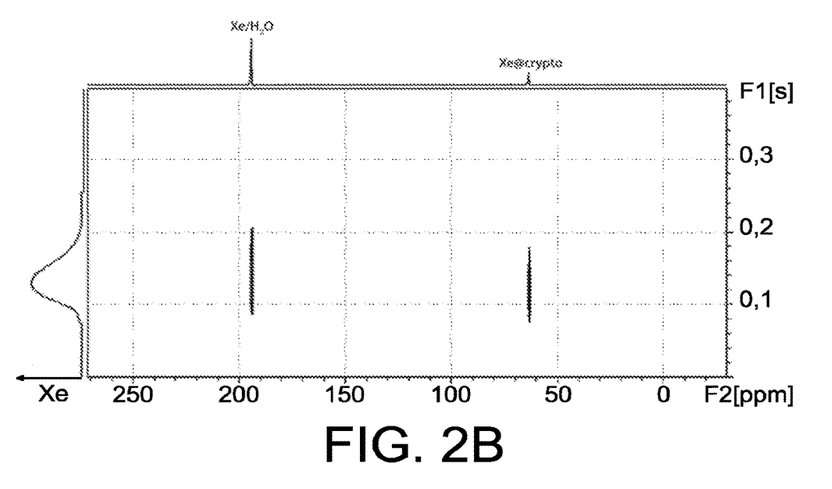

FIGS. 2A and 2B show NMR measurements corresponding to two measurements made on a solution of cryptophanes during introduction of hyperpolarised xenon. Each of these measurements show the variation of the NMR signal with the quantity of hyperpolarised xenon, the variation in the quantity of hyperpolarised xenon being illustrated graphically on the left part of the figures. The different NMR peaks detected during these measurements are reproduced on the top part of these figures.

During the measurements reproduced in FIG. 2A, gas is introduced according to a method known in prior art that consists of dissolving hyperpolarised xenon in solution 33 by stirring. It can be seen on this first spectrum that peaks of dissolved xenon (Xe/H2O) encapsulated in cryptophanes (Xe@crypto) are accompanied by a xenon gas peak (Xegas) thus demonstrating that dissolution is only partial. The NMR measurement using this method according to prior art is therefore disturbed by the introduction of hyperpolarised xenon during the measurement. In FIG. 2B, hyperpolarised xenon is introduced using a cell according to the principle of the invention. It can be seen that with the use of a measurement cell 20 according to the invention, although dissolved xenon peaks (Xe/H2O) reacting with cryptophanes (Xe@crypto) are also observed, no xenon gas peak is observed. This shows that a measurement cell 20 can efficiently introduce gas without this introduction disturbing the NMR measurement.

Therefore, such a measurement cell 20 can be installed in an NMR spectrometer according to the configuration shown in FIG. 1A. In this configuration, after the solution 33 to be measured has been introduced in the measurement cell 20, the measurement cell is placed in the corresponding housing with its base bearing on the bottom part of said housing. The gas conveyance conduit and the gas outlet are both connected to a gas supply network and the radiofrequency system is connected to the NMR spectrometer so as to enable generation and/or measurement of a radiofrequency electromagnetic field in the measurement chamber of the spectrometer.

The NMR spectrometer and the solution thus form a Nuclear Magnetic Resonance measurement assembly.

It should be noted that such an assembly is particularly suitable for measuring a solution with introduction of gas with non-equilibrium magnetic properties, such as a hyperpolarised xenon or helium gas 3 that requires the static magnetic field of the NMR spectrometer to prolong the life of this state. Nevertheless, its application is not limited to this type of measurement. The measurement cell 20 is perfectly suitable for the introduction of any type of gas during an NMR measurement regardless of the purpose of this introduction. Such a cell can thus be used for measurements in which:

- the gas is used to supply the solution, for example oxygen in a biological solution;
- the gas interacts with the solution, for example like the above-mentioned polarisation;
- the gas acts as a vector for an additive to be added into the solution;
- the gas itself is to be measured.

According to other application possibilities, the measurement cell 20 has another advantage in addition to the possibility of introducing a gas without disturbing the NMR measurement, in that it can reduce the quantity of solution 33 necessary for the NMR measurement because there is no need for a network of conduits outside the detection volume.

Another application of the measurement cell 20 according to the invention is to introduce gas only to set up circulation of the solution in the cell itself. According to this possibility, the objective is to circulate the solution in the network of conduits and therefore to circulate the solution in the measurement chamber to prevent stagnation of the solution in the measurement chamber.

Thus, the measurement cell 20 may also be used in the study of atoms in the liquid phase in which nuclei relax slowly. This type of study applies to many isotopes and compounds including:

- organic molecules comprising carbon or nitrogen atoms not coupled to hydrogen atoms;
- nuclei that do not have a very efficient intrinsic relaxation mechanism (for example such as the quadrupolar relaxation), and
- nuclei for which longitudinal relaxation is long while transverse relaxation is short (case of atoms in large molecules or molecular assemblies for which the reorientation time in the field is long).

In the measurement cell 20 according to the invention, only atoms present in the measurement zone are excited by the radiofrequency and are detected. During such measurements, it is necessary to wait for their relaxation to detect them again. Thus, circulation according to the invention can continuously renew atoms present in the measurement zone by replacing excited atoms by atoms that are disexcited during their circulation in the network of conduits. Sequences can thus be performed much faster by drastically reducing the repetition time between two NMR measurements that then becomes independent of the nucleus relaxation time.

Figure 3:
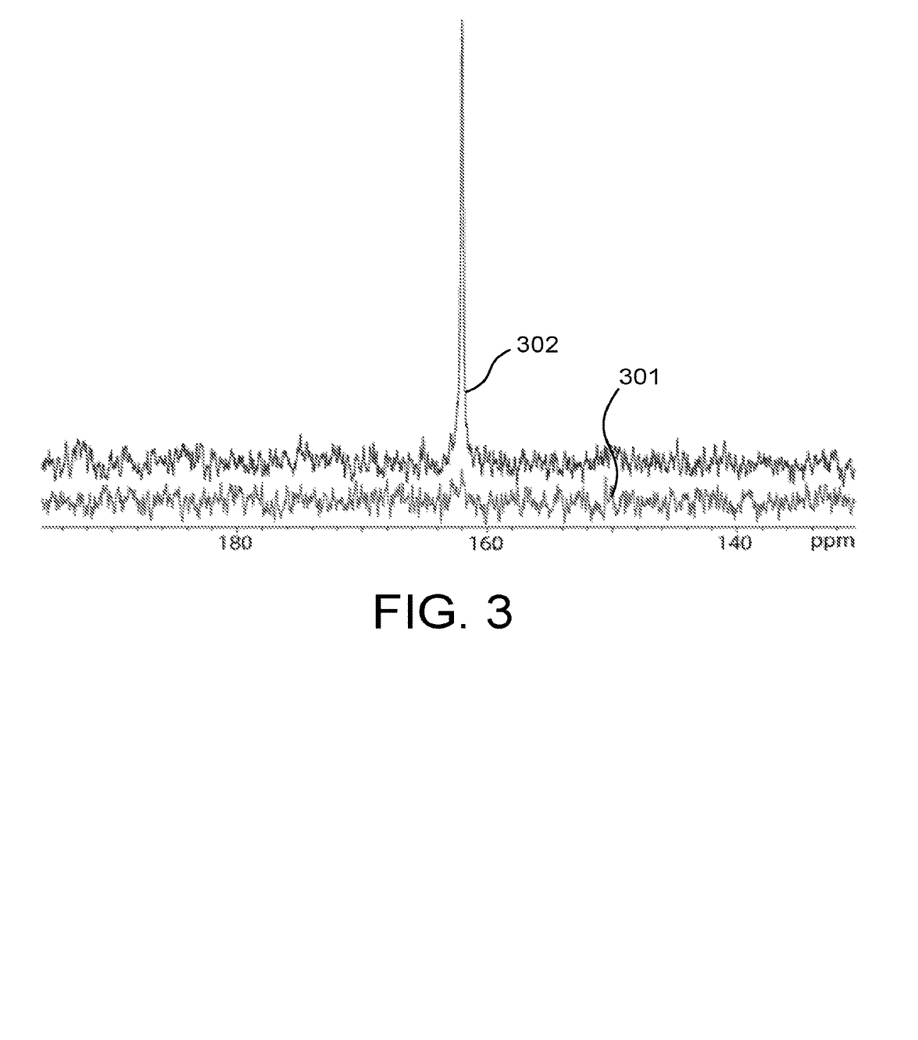
FIG. 3 graphically illustrates the results obtained with an application of the invention with the objective of circulating the solution in the cell.

FIG. 3 thus illustrates this possibility during a measurement made on a solution of urea, of which 99% of the molecules comprise the carbon 13 isotope at a concentration of 200 mmol·$L^{-1}$ in water. FIG. 3 thus illustrates the NMR signal measured without circulation 301 and with circulation 302 in the network of conduits obtained by introducing a gas flow of 1 ml·$min^{-1}$. Experimental conditions are identical during these two measurements and are as follows:

- static magnetic field equal to 11.74 Tesla,
- coil system 222 tuned to 125.76 MHz,
- 16 acquired NMR measurements, preceded by 2 measurements without acquisition,
- repetition time between two NMR measurements equal to 2 seconds.

It can thus be seen that if there is no circulation of the solution, the graphic (reference 301) shows that the signal is of the same order of magnitude as the background noise while putting the fluid into circulation makes it possible to recover a peak corresponding to the carbon 13 isotope with a higher intensity than is obtained without fluid circulation. The signal to noise ratio is thus very much better than it is with a measurement in which the solution is static.

Figures 4A, 4B:
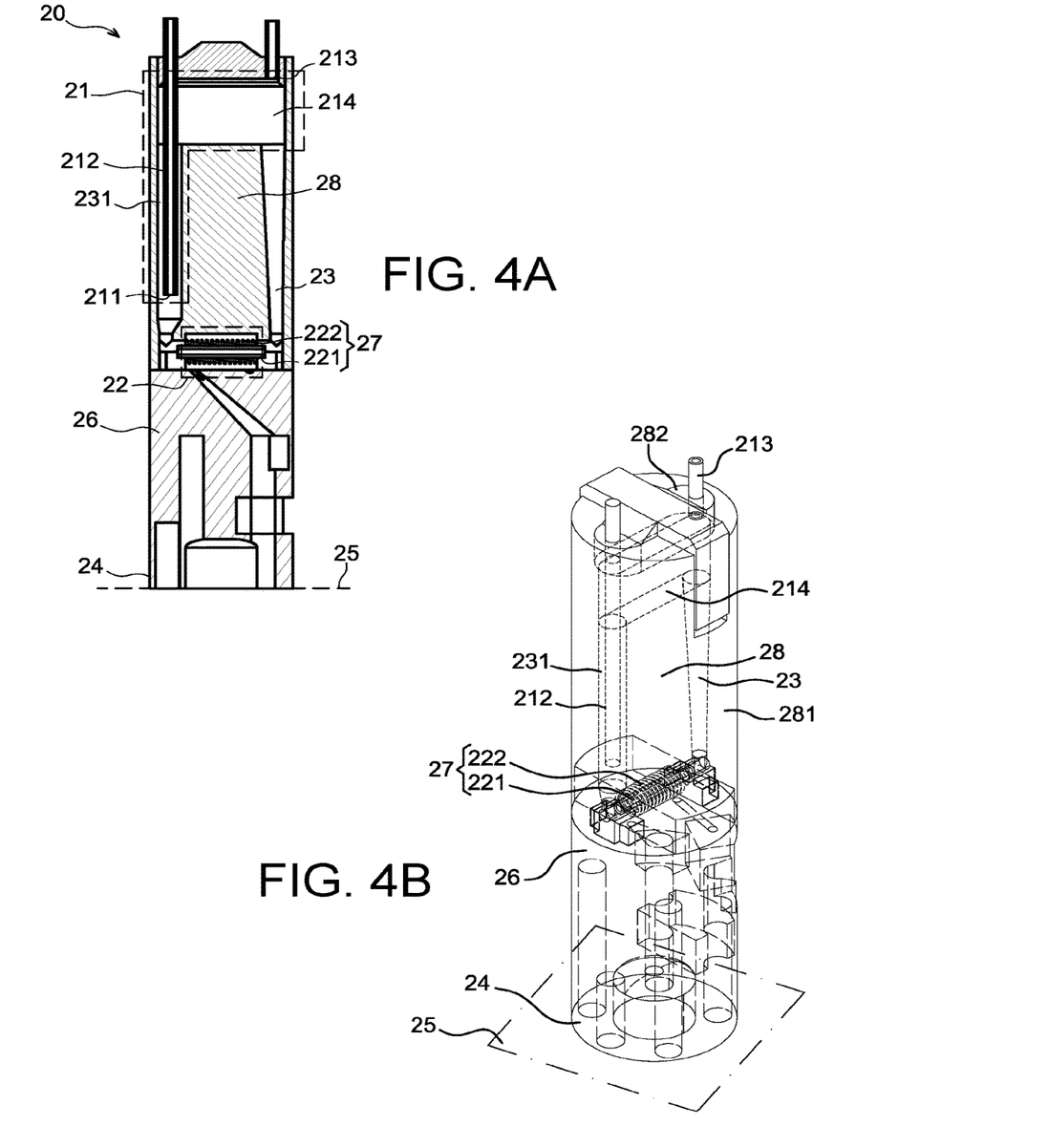
FIGS. 4A and 4B show a sectional view and a three-quarter view respectively, with some of the elements shown transparently in FIG. 4B.

FIGS. 4A and 4B show a sectional view and a perspective view of a measurement cell 20 according to a first practical design based on the principle of the invention illustrated in FIG. 1A.

The measurement cell 20 shown in FIGS. 4A and 4B comprises a casing made in two portions 26, 27, 28, a first portion 26, 27 forming the base for installation of the measurement cell 20 in the housing of the NMR spectrometer and in which the measurement chamber 21 is formed, and a second portion 29 comprising the gas introduction zone, said first and second portions being complementary in shape, such that the network of conduits 23 is formed by the assembly of the first and the second portions 26, 27, 28. The first portion 26, 27 comprises a first and a second element 26, 27, the first element 26 forming the outside envelope of the first portion 26, 27, the second element 37 comprising the measurement chamber 22.

Thus, it can be seen in FIGS. 4A and 4B, that the measurement cell is generally cylindrical in shape, the first portion 26, 27 representing the lower part and second portion 28 representing the upper part.

The lower surface of the first portion 26, 27 delimits the base plane 25 on which the cell will be supported in a housing in the NMR spectrometer 1. The first element 26 represents the larger part of the first portion 26, 27 and is shaped so that the measurement cell 20 fits well into the corresponding housing in the NMR spectrometer. Thus, the first element 26 comprises orifices shaped to cooperate with devices for placement of the housing in the NMR spectrometer. The first element also comprises a recess at the top for placement of the second element and passages adapted to supply the coil system 222 of the second element 27. In one practical embodiment, the first element 26 may be made from a plastic material such as, non-limitatively, Polymethyl methacrylate (PMMA), Acrylonitrile butadiene styrene (ABS), and Polypropylene (PP). Obviously, other materials such as glass and ceramic could be envisaged for making the first element 26.

The second element 27 comprises a conduit 221 in the network of conduits 23 of the measurement cell 20, this conduit 221 preferably being adapted to be neutral relative to the NMR measurement, and the coil system 222 to generate an electromagnetic field in said conduit. Therefore the second element is positioned in the recess of the first element with the two ends of its conduit open so as to be able to cooperate with the remainder of the network of conduits formed in the second portion 28. In a practical embodiment, the second element 27 may be formed for example by a glass or quartz tube around which the coil system 222 is mounted. The risks of disturbance to the NMR measurement due to the walls of the NMR measurement chamber are strongly reduced with such materials.

The second portion 28 comprises the remaining part of the network of conduits 23 and the gas introduction zone 21, the gas introduction conduit 231 being formed in it. The second portion 28 is in the form of a central structure 281 in which conduits in the network of conduits 23 other than the conduit included in the second element are formed. Thus, in FIGS. 4A and 4B, it can be seen that the second portion comprises two conduits approximately perpendicular to the base plane 25, including the gas introduction conduit and the first part 214a of the gas extraction area 214 that extends approximately parallel to the base plane 25. In one practical embodiment, this vertical structure 281 can be made from a plastic material such as (non-limitatively) Polymethyl methacrylate (PMMA), Acrylonitrile butadiene styrene (ABS), and Polypropylene (PP). Obviously, other materials such as glass and ceramic can also be envisaged for making the vertical structure 281.

The second portion 28 also comprises a gas conveyance conduit 212 and a conduit forming the gas outlet 213. These two conduits extend approximately perpendicular to the base plane 25, the first in the gas introduction conduit 231, the second in the extraction area, and both have one end that projects from the vertical structure 281 so that they can be connected to a gas supply network 32.

In this practical design, the second portion 28 comprises a closing part 282 in which the upper part of the gas conveyance conduit 212 and the conduit forming the gas outlet 213 are housed and that closes off the gas extraction area 214. In one practical embodiment, this closing part 282 may be made from a plastic material such as, non-limitatively, Polymethyl methacrylate (PMMA), Acrylonitrile butadiene styrene (ABS), and Polypropylene (PP). Obviously, other materials such as glass and ceramic could also be envisaged for making the closing part 282.

A measurement cell 20 according to this practical design has the advantage that it can be manufactured at low cost because of the materials that can be used. Therefore, it is possible to design a single-use cell thus preventing any risk of contamination inherent to the reuse of measurement cells. It should also be noted that its design makes it compatible with three-dimensional printing technologies (fast prototyping or additive technologies) thus correspondingly reducing low quantity manufacturing costs, while enabling fast prototyping for easy adaptation to technological constraints.

Such a measurement cell can be manufactured making use of a manufacturing method including the following steps:
provide the second portion 28 so as to provide the network of conduits 23, excluding a conduit 221 inside the measurement chamber 22, the gas inlet 211 being positioned in said network of conduits 23;
provide the first element 26 of the first portion 26, 27;
provide the second element 27 of the first portion 26, 27 so as to provide the conduit 221 included in the measurement chamber 22 and a coil system 222 to generate a radiofrequency electromagnetic field;
assemble the first and the second element 26, 27 of the first portion 26, 27 to form the first portion 26, 27;
assemble the first and the second portion 26, 27, 28 to form the measurement cell 20, this assembly being used to connect the network of conduits 23, excluding the conduit 221 forming the measurement chamber 22, with the conduit 221 inside the measurement chamber 22 and form the network of conduits 23.

Figure 5A:
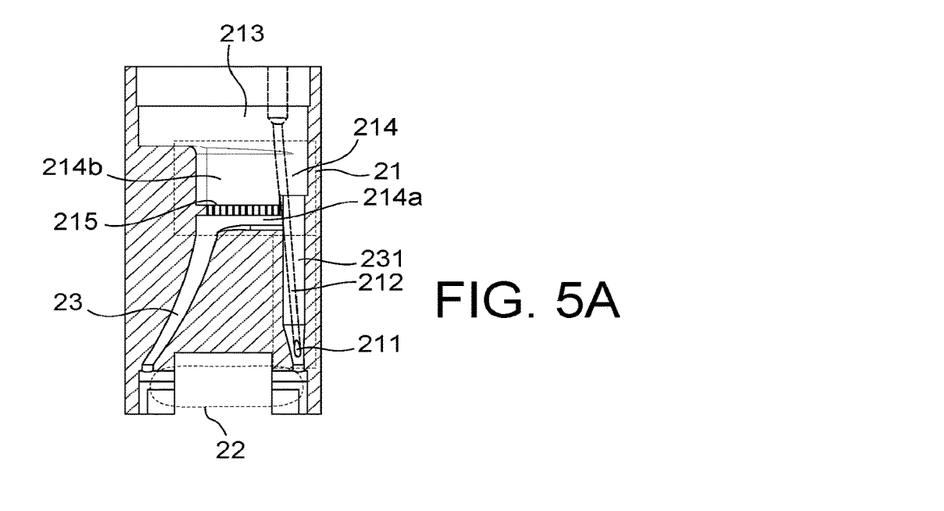
FIGS. 5A and 5B show an NMR cell according to a second embodiment adapted to enable a higher solution circulation velocity, FIG. 5A illustrating a cross-sectional view of the upper part of said NMR cell and FIG. 5B illustrating a three-quarter view of this NMR cell.
Figure 5B:
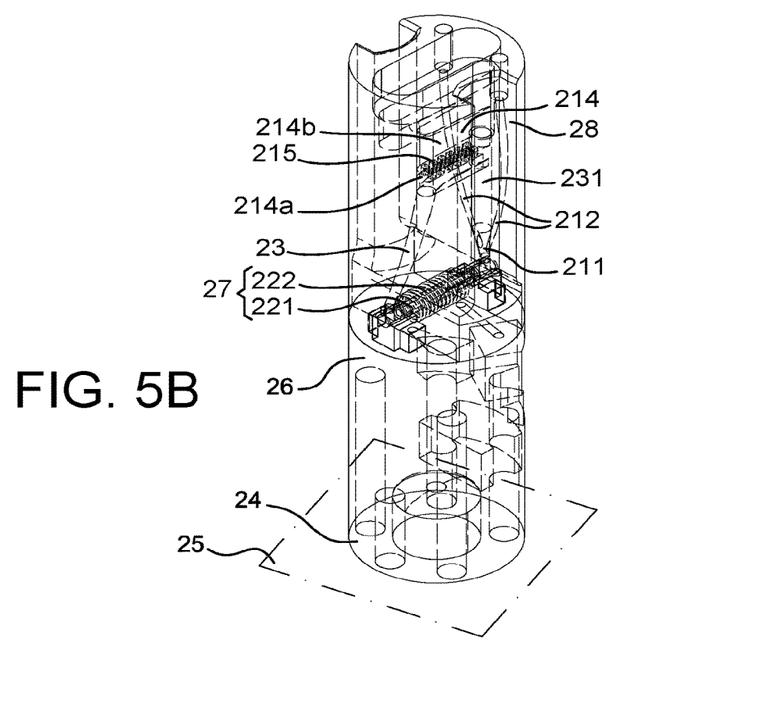

FIGS. 5A and 5B show a measurement cell according to a second practical design based on the principle according to the invention in which the measurement cell 20 includes a filtration system in the gas introduction zone, to filter the bubbles. A measurement cell 20 according to this second practical design is different from the measurement cell in the first practical design in that the filtration system is included in the gas extraction area 214 and in that the conveyance conduit 212 is not housed in the gas introduction conduit but rather in two peripheral conduits opening up in the gas introduction conduit.

Thus, the measurement cell 20 according to this second practical design is different from the first practical design only in its second portion 28, the first portion 26, 27 being identical to the first portion of the measurement cell according to the first practical design. This is why FIG. 5A only shows this second portion 28.

The second portion 28 of the measurement cell according to this second design includes a filtration grid 215 in the gas extraction area 214 with a mesh adapted to filter the solution as it passes from the gas introduction zone 21 into the conduits in the network of conduits 23 conveying the solution to the measurement chamber 22.

The filtration grid 215 is configured to retain any gas bubbles that might be carried outside the gas introduction zone due to fast circulation of the solution. To achieve this, the mesh size of the filtration grid 215 is smaller than the minimum size of bubbles generated in the gas introduction zone. Thus for example, the mesh of the filtration grid 215 may be chosen to be smaller than 1 mm and equal to approximately 0.5 mm or even 0.25 mm. The diameter of gas bubbles is usually 2 to 3 mm.

The filtration grid 215 is located in the gas extraction area 214 so as to intercept the solution as it circulates in the gas introduction zone towards the measurement chamber. Such an arrangement is provided by the gas introduction conduit opening up into an upper portion of the first part 214a of the extraction area 214, the conduit connecting the extraction area 214 to the measurement chamber 22 being in fluidic communication with the extraction area 214 on a lower portion of the first part 214a of the extraction area 214, and the filtration grid 215 being arranged to be interposed between the upper portion and the upper portion to intercept the solution as it passes between these two portions.

With such a configuration, the filtration grid 215 forms a filtration system positioned in the network of conduits to intercept gas bubbles at the outlet from the gas introduction zone along the direction of circulation of the solution.

Obviously, although the filtration system in this second practical design consists of a filtration grid, it can also be formed by any other type of filtration system without going outside the scope of the invention. Thus, it would be perfectly possible to provide a filtration foam in the extraction zone adapted to filter bubbles, instead of a filtration grid, or even to use a plurality of conduits with a sufficient small diameter to prevent the circulation of bubbles towards the measurement chamber 22.

Another special feature of this cell according to this second practical design is that the second portion 28 comprises one or two gas conveyance conduits 212 supplying two gas inlets 211 in the gas introduction conduit 231. Furthermore, the two conveyance conduits 212 are two peripheral conduits. In this way, the conveyance conduits 212 thus integrated in the second portion 28 do not create any obstacle to circulation of the solution in the conduit circuit 23; avoiding head losses that would be induced by the volume occupied by the gas conveyance conduit. It should also be noted that the presence of the two gas inlets 211 makes it possible to use two different gases, such as a gas with non-equilibrium magnetic properties and oxygen to supply cells. This can increase the gas quantity introduced.

As a variant, one of these two gas inlets 211 can be used for example to introduce a liquid to compensate for any evaporation, rather than for introducing a gas. Similarly, these two gas inlets 211 could also be used to increase the introduced gas flow and also the circulation velocity of the solution. Such an increase in the quantity of gas introduced and the circulation velocity does not increase risks of gas bubbles being present in the measurement chamber 22, due to the presence of the filtration grid 215.

It should be noted that in the embodiment and practical designs described above, the entire measurement cell can be contained within the static magnetic field of the NMR spectrometer in which it is installed, during an NMR measurement. Nevertheless, it could also be possible for only part of the volume of the cell to be contained within the static magnetic field of the NMR spectrometer, without going outside the scope of the invention, said part being called the detection volume. According to this possibility of the invention, the measurement cell then includes the gas introduction zone and the measurement chamber in said detection volume, with at least part of a network of conduits bringing the gas introduction zone into fluid communication with the measurement chamber.

Similarly, in the embodiment and practical designs described below, the solution 33 to be measured is circulated only by the gas introduced into solution 33. Nevertheless, without going outside the scope of the invention, it would be possible that fluid circulation in the network of conduits could be achieved by another means complementary to or instead of the introduction of gas. Thus, for example, it would be possible to provide a fluid circulation system such as a syringe system or a syringe push system or a peristaltic pump.

Finally, measurement cells according to the embodiment and practical designs described above only include one measurement chamber, for simplification reasons. Obviously, without going outside the scope of the invention, it would also be possible to use several measurement chambers, within the size limits for the NMR spectrometer to be equipped.

The invention claimed is:

1. A Nuclear Magnetic Resonance (NMR) measurement cell in solution enabling the introduction of a gas into said solution, the measurement cell being designed to be placed in a static magnetic field such as the field of an NMR spectrometer, and comprising:
   at least one measurement chamber of the solution in which a radiofrequency electromagnetic field will be applied and/or measured,
   a network of conduits including a gas introduction zone, the gas introduction zone comprising a gas inlet to generate bubbles only in the gas introduction zone, the network of conduits forming a closed loop circuit for circulation of the solution between the measurement chamber and the gas introduction zone, the gas inlet being arranged so as to set up circulation of the solution in the network of conduits between the gas introduction zone and the measurement chamber, the measurement chamber comprising a conduit in the network of conduits called the measurement conduit, and
   a radiofrequency system arranged to apply and/or detect a radiofrequency electromagnetic field in the measurement conduit.

2. Measurement cell according to claim 1, in which the gas introduction zone also comprises a gas outlet in fluidic communication with the network of conduits in a part of the network of conduits that is configured to be empty of the solution when the measurement cell is filled with the solution.

3. Measurement cell according to claim 2, in which the measurement chamber is configured such that a ratio between a circulation distance of the solution from the measurement chamber to the gas inlet and a circulation distance from the gas outlet to the measurement chamber in conduit circuit of the measurement chamber is less than 1.

4. Measurement cell according to claim 2, in which the measurement cell comprises a base for installation in an NMR spectrometer defining a base plane, and in which the gas introduction zone comprises a gas introduction conduit, in the network of conduits, that extends transverse or approximately perpendicular to the base plane, the gas inlet being located in the gas introduction conduit closer to the base than the gas outlet.

5. Measurement cell according to claim 4 comprising a gas conveyance conduit in the gas introduction conduit, a first end of the gas conveyance conduit opens up into the gas introduction conduit and forms the gas inlet.

6. Measurement cell according to claim 4, in which the gas introduction conduit opens up into a gas extraction area of which a first part delimits a conduit in the network of conduits and a second part is outside of the solution, the gas outlet being located in said second part.

7. Measurement cell according to claim 1 comprising a casing made in two portions, a first portion forming a base for installation of the measurement cell in an NMR spectrometer and in which the measurement chamber is formed, and a second portion comprising the gas introduction zone, said first and second portions having complementary shapes such that the network of conduits is formed by the assembly of the first and the second portion.

8. Measurement cell according to claim 7, in which the first portion comprises a first and a second element, the first element forming an external casing of the first portion, the second element comprising the measurement chamber and the radiofrequency system.

9. Measurement cell according to claim 1 also comprising a filtration system in the gas introduction zone formed in the network of conduits to intercept gas bubbles at an outlet from the gas introduction zone along a direction of circulation of the solution.

10. Measurement cell according to claim 9 in which the filtration system comprises a filtration grid with a mesh size smaller than 1 mm.

11. A Nuclear Magnetic Resonance (NMR) measurement cell in solution enabling the introduction of a gas into said solution, the measurement cell being designed to be placed in a static magnetic field such as the field of an NMR spectrometer, and comprising:
   a base for installation in an NMR spectrometer defining a base plane,
   at least two conduits, a first conduit called a gas introduction conduit, and a second conduit, both extending transversally to the base plane, the gas introduction conduit comprising a gas inlet to form bubbles in the first conduit and thus form a gas introduction zone,
   at least a third and a fourth conduit connecting the first and second conduits at their ends located close to the base and at a distance from the base respectively, so as to form a network of conduits, the network of conduits forming a closed loop circulation circuit for the solution between a measurement chamber and the gas introduction zone, and a radiofrequency system formed in the measurement chamber to apply and/or detect a radiofrequency electromagnetic field in a portion of the third conduit.

12. A method of manufacturing a measurement cell, comprising:

providing a radiofrequency system;

providing a conduit in which measurement will be made, to form a measurement conduit;

positioning the radiofrequency system relative to the measurement conduit such that the radiofrequency system can apply and/or detect a radiofrequency electromagnetic field in the measurement conduit so as to form a measurement chamber;

providing additional conduits to form a network of conduits with the measurement conduit, the additional conduits comprising a gas introduction zone comprising a gas inlet to generate bubbles only in the gas introduction zone; and forming the measurement cell by assembling the additional conduits with an assembly formed during positioning of the radiofrequency system relative to the measurement conduit, the network of conduits forming a closed loop circuit for circulation of solution between the measurement chamber and the gas introduction zone, the gas inlet being arranged so as to set up circulation of the solution in the network of conduits between the gas introduction zone and the measurement chamber.

13. Manufacturing method according to claim 12 in which:

the providing the additional conduits to form the network of conduits with the measurement conduit comprises providing the network of conduits, excluding a conduit inside the measurement chamber, the gas inlet being formed in said network of conduits, said additional conduits forming a first element, the positioning the radiofrequency system relative to the measurement conduit comprises forming a second element including the conduit inside the measurement chamber and a radiofrequency system capable of generating and/or measuring a radiofrequency field, the forming the measurement cell comprises assembling the first element including the network of conduits, excluding the conduit inside the measurement chamber, with the second element including the conduit inside the measurement chamber.

14. A Nuclear Magnetic Resonance (NMR) measurement assembly for use with a solution comprising:

an NMR spectrometer configured to generate a first static magnetic field;

an NMR measurement cell in solution;

a gas introduction system; and the NMR measurement cell being a cell according to claim 1 with its gas inlet connected to the gas introduction system.

* * * * *